(12) United States Patent
Scott

(10) Patent No.: US 6,271,370 B1
(45) Date of Patent: Aug. 7, 2001

(54) PROCESS FOR THE SYNTHESIS OF NUCLEOSIDE ANALOGS

(75) Inventor: Robert W. Scott, Mystic, CT (US)

(73) Assignee: Pfizer INC, New York, NY (US)

(*) Notice: Subject to any disclaimer, the term of this patent is extended or adjusted under 35 U.S.C. 154(b) by 0 days.

(21) Appl. No.: 09/566,468

(22) Filed: May 8, 2000

Related U.S. Application Data

(60) Provisional application No. 60/133,651, filed on May 11, 1999.

(51) Int. Cl.$^7$ .................................................. C07H 19/14
(52) U.S. Cl. ........................................... 536/27.11; 536/124
(58) Field of Search ................................ 536/27.11, 124

(56) References Cited

U.S. PATENT DOCUMENTS

| | | | |
|---|---|---|---|
| 4,751,292 | 6/1988 | Fox | 536/24 |
| 4,859,677 | 8/1989 | Borchardt et al. | 514/261 |
| 5,110,926 | 5/1992 | Storer et al. | 544/276 |
| 5,246,931 | 9/1993 | Norbeck et al. | 514/242 |
| 5,605,903 | 2/1997 | Borcherding et al. | 514/258 |
| 5,674,998 | 10/1997 | Boyer et al. | 536/27.13 |
| 5,693,771 | 12/1997 | Alexander et al. | 536/18.6 |
| 5,726,174 | 3/1998 | Kim et al. | 544/244 |
| 5,744,596 | 4/1998 | Mansour et al. | 536/27.11 |
| 5,747,473 | 5/1998 | Classon et al. | 514/45 |
| 5,763,596 | 6/1998 | Boyer et al. | 536/27.13 |
| 5,808,147 | 9/1998 | Daluge et al. | 562/504 |
| 5,830,881 | 11/1998 | Lin et al. | 514/45 |
| 5,837,871 | 11/1998 | Kim et al. | 544/243 |
| 5,840,743 | 11/1998 | Townsend et al. | 514/395 |
| 5,852,027 | 12/1998 | Liotta et al. | 514/274 |

FOREIGN PATENT DOCUMENTS

| | | |
|---|---|---|
| 9604293 * | 2/1996 | (WO) . |
| 9640705 | 12/1996 | (WO) . |

OTHER PUBLICATIONS

Scott, "β–Selective Nucleoside Analog Synthesis from Chlorofuranoses," *Tetrahedron Letters*, 41, 8207–8210 (2000). Copy supplied by applicant.*

Seela et al., "2,4–Disubstituted Pyrrolo[2,3–d]pyrimidine α–D and β–D–Ribofuranosides Related to 7–Deazaguanosine," *Helvetica Chimica Acta*, 73(7), 1879–1887 (Oct. 31, 1990).*

Ramasamy et al.(I), "Total and Sterospecific Synthesis of Cadeguomycin, 2'–Deoxycadeguomycin, ara–Cadeguomycin, and Certain Related Nucleosides," *Journal of the Chemical Society* Perkin Transaction I, (Issue No. 12), 2375–2384 (Dec., 1989).*

Sanghvi et al., "Synthesis and Biological Evaluation of Certain C–4 Substituted Pyrazolo[3,4–b]pyridine Nucleosides," *Journal of Medicinal Chemistry*, 32(5), 945–951 (May, 1989).*

Cristalli et al., "3,7–Dideazapurine Nucleosides. Synthesis and Antitumor Activity of 1–Deazatubercidin and 2–Chloro–2'–deoxy–3,7–dideazaadenosine," *Journal of Medicinal Chemistry*, 32(7), 1463–1466 (Jul., 1989).*

Ramasamy et al.(II), "A Facile and Improved Synthesis of Tubercidin and Certain Related Pyrrolo[2,3–d]pyrimidine Nucleosides by the Stereospecific Sodium Salt Glycosylation Procedure[1]," *Journal of Heterocyclic Chemistry*, 25, 1893–1898 (Nov./Dec., 1988).*

Rosemeyer et al., "Stereoselective Synthesis of Pyrrolo[2, 3–d]pyrimidine α– and β– D–Ribonucleosides from Anomerically Pure D–Ribofuranosyl Chlorides: Solid–Liquid Phase–Transfer Glycosylation and $^{15}$N–NMR Spectra," *Helvetica Chimica Acta*, 71(6), 1573–1585 (Sep. 28, 1988).*

Ramasamy et al.(III), "A Facile Synthesis of Tubercidin and Related 7–Deazapurine Nucleosides Via the Sterospecific Sodium Salt Glycosylation Procedure," *Tetrahedron Letters*, 28(43), 5107–5110 (1987).*

Cupps et al., "A Novel Three–Step Synthesis of a Pyrrolo [3,2–d]pyrimidine C–Nucleoside," *Journal of Organic Chemistry*, 51(7), 1058–1064 (Apr. 4, 1986).*

Kondo et al., "A Total Synthesis of Cadeguomycin, a Nucleoside Antibiotic Produced by Streptomyces Hygroscopicus," *Tetrahedron*, 42(1), 199–205 (1986).*

Cottam et al., 1984, J. Med. Chem. 27:1119–1127, "Synthesis and biological activity of certain 3,4–disubstituted pyrazolo[3,4–d]pyrimidine nucleosides."

Ireland et al., 1978, J. Org. Chem. 43:786–787, "An efficient method for the preparation of furanoid and pyranoid glycals."

Lerner, 1969, J. Org. Chem. 34(1):101–103, "Preparation of nucleosides via isopropylidene sugar derivatives. IV. Synthesis of 9–α– and 9–β–L–erythrofuranosyladenine."

Lerner, 1969, Carbohdr. Res. 9:1–4, "A simple alternative synthesis of L–erythrose."

Wilcox et al., 1986, Tetrahedron Lett. 27:1011, "Steroselective preparations of ribofuranosyl chlorides and ribofuranosyl acetates. Solvent effects and stereoselectivity in the reaction of ribofuranosyl acetates with trimethylallylsilane."

* cited by examiner

Primary Examiner—James O. Wilson
Assistant Examiner—L. Eric Crane
(74) Attorney, Agent, or Firm—Peter C. Richardson; Paul H. Ginsburg; Alan L. Koller

(57) ABSTRACT

The present invention relates to an improved method for synthesizing nucleosides with a low α:β anomeric ratio. The method comprises coupling a protected furanosyl halide and an appropriately protected heterocycle in the presence of a nucleophilic polar solvent and a strong base.

20 Claims, No Drawings

PROCESS FOR THE SYNTHESIS OF NUCLEOSIDE ANALOGS

This Appln claim benefit of Prov. No. 60/133,651 filed May 11, 1999.

FIELD OF THE INVENTION

The present invention is within the field of synthetic organic chemistry. In particular, it relates to an improved process for the synthesis of β-nucleosides or β-nucleoside analogs based upon an improved coupling reaction between a heterocycle and a furanosyl halide.

BACKGROUND OF THE INVENTION

Nucleoside analogs are an important class of compounds that have potential utility as treatments for a variety of diseases. Some nucleoside analogs may be efficacious because of their ability to inhibit adenosine kinase. Adenosine kinase catalyzes the phosphorylation of adenosine to adenosine 5'-monophosphate (AMP). Inhibition of adenosine kinase may effectively increase the extracellular level of adenosine in humans and thereby potentially serve as a treatment of ischemic conditions such as stroke, inflammation, arthritis, seizures, and epilepsy. See e.g. U.S. Pat. No. 5,674,998. Nucleoside analogs may also have potential for the treatment of chronic pain. However, in order to conduct clinical trials to determine the clinical efficacy of nucleoside analogs as well as meet the demand once the therapy is brought to the market, scaled-up quantities of the purified nucleoside analog of interest are necessary.

The nucleoside analogs that can be synthesized by the process of this invention consist of a furanose covalently bound to a heterocycle (B) as represented by the following formula:

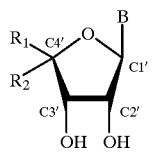

The substitutents at the C4' position of the furanose ring, $R_1$ and $R_2$, can be optionally and independently substituted by groups such as $(C_1-C_6)$ alkyl or substituted $(C_1-C_6)$ alkyl. If $R_1$ is —$CH_2$—OH and $R_2$ is —H, then the nucleoside sugar is ribose. The furanose contains an anomeric carbon (at position C1'). Because of the anomeric carbon, there are two stereoisomers, or anomers, of furanose: the α-anomer and the β-anomer. See e.g. Streitweiser and Heathcock, 1985, *Introduction to Organic Chemistry*, Macmillan. The stereoisomerism of furanose results in corresponding α and β nucleoside isomers. Typically, the β-nucleoside anomer is the anomer of biological interest.

The synthesis of pure β-nucleosides and β-nucleoside analogs has proven to be difficult. Many published schemes for nucleoside analog synthesis result in α:β anomeric mixtures. Typically, it is difficult to isolate the β-anomer from such α:β mixtures, especially if economical scaled-up quantities of pure β-nucleoside analog are required. To avoid undesirable α:β nucleoside analog mixtures, the art has emphasized the use of starting reagents that favor the production of β-nucleoside analogs over α-nucleoside analogs. The prior art can be divided into three categories (i) heavy metal approaches (ii) α-furanosyl halide approaches, and (iii) a sodium hydride/N,N-dimethylformamide based approach.

The heavy metal approaches use a heteroanion coupled with a heavy metal such as mercury or silver. For example, Lerner was able to use a heavy metal approach to produce yields of 9-(α,β)-L-erythrofuranoslyadenine in which the β-anomer predominated over the α-anomer by a ratio of almost thirty to one. Lerner, 1969, *Carbohydr. Res.*, 9, 1–4. In the Lerner method, a chloromercuriheterocycle complex was reacted with a β-furanosyl chloride in the presence of a hot hydrocarbon solvent to yield the nucleoside analog. This reaction was driven by the formation of mercuric dichloride salt. Because of the toxicity of mercury, the Lerner approach is not optimal for large-scale synthesis of β-nucleosides. However, it is well known in the art that silver can often be used instead of mercury in reactions such as those provided by Lerner et al. Thus the toxicity of mercury can be avoided.

In general, the heavy metal approaches are generally adequate but less than satisfactory in practice. Stoichiometric quantities of heavy metal, relative to the sugar or the heterocycle, are required. In scaled-up reactions, the use of 1:1 molar ratios of heavy metal to heterocycle anion is expensive and typically does not provide an economical solution for the stereospecific synthesis of biologically active nucleoside analogs. Furthermore, in the case of some nucleoside analogs of interest, the heavy metal approaches often fail altogether.

The α-furanosyl halide approaches use α-furanosyl halide as a starting reagent. In such approaches, an inversion at the anomeric center of the α-furanosyl chloride occurs upon coupling of the furanosyl with a heteroanion. For example Ramasay et al. stereospecifically synthesized β-7-deazaguanosine and related nucleoside analogs using an α-furanosyl halide approach. Ramasay et al., 1987, *Tetrahedron Letters*, 28, 5107–5110. The method of Ramasay et al. is illustrated in scheme (I):

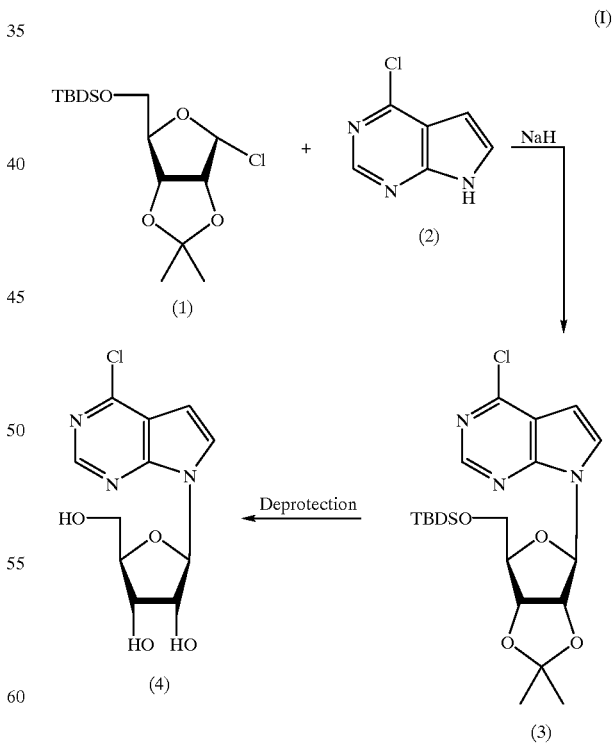

where TBDS represents t-butyldimethylsilyl. In reaction scheme (I), the sodium salt of heterocycle (2) was generated by treatment with sodium hydride (NaH) in acetonitrile and then reacted with α-furanosyl chloride (1) to afford protected β-nucleoside analog (3). The protected β-nucleoside analog (3) was then deprotected to yield β-nucleoside (4). The α-furanosyl chloride (1) may be prepared according to the methods of Wilcox et al., 1986, *Tetrahedron Lett.*, 27, 1011.

Like the heavy metal approaches, the α-furanosyl halide methods are functional but not always satisfactory in practice. For instance, such methods are not always amendable to scale-up because the α-furanosyl halide starting material is typically unstable and rapidly isomerizes to the β-isomer. Furthermore, the α-furanosyl halide is more difficult to form than the β-furanosyl halide anomer. For instance, special reaction conditions, such as low temperatures, are typically needed to synthesize the α-furanosyl halide. For these reasons, approaches that use a β-furanosyl halide anomer as a starting reagent are preferred over α-furanosyl halide approaches.

The sodium hydride/N,N-dimethylformamide approach does not involve the use of heavy metals or α-furanosyl halides. Kondo et al., 1986, *Tetrahedron*, 42, 199–205. In Kondo, an α:β mixture of nucleoside analog (8) was synthesized by coupling β-furanosyl chloride (5) with the heterocycle anion of (6) to yield the protected β-nucleoside analog (7) according to scheme (II):

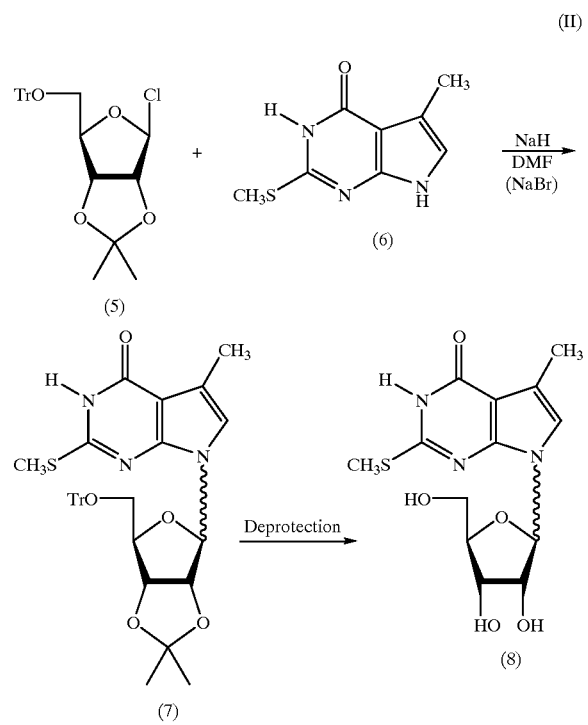

wherein Tr represents trityl and DMF represents N,N-dimethylformamide. The protected β-nucleoside analog (7) was then deprotected using standard methods to yield the β-nucleoside analog (8). Kondo et al. found that the coupling of the β-furanosyl chloride (5) with heterocycle (6) in the presence of sodium hydride and DMF resulted in a highly undesirable 3:1 mixture of (α,β)-nucleoside analog (8). To improve the α:β anomeric selectivity, Kondo et al. experimented with the use of NaBr, NaI, MgBr$_2$OEt$_2$, or (n-Bu)$_4$NBr as additives to reaction (II). The best results that Kondo et al. obtained based upon this experimentation was a 1:2 α:β mixture of nucleoside analog (8) when the coupling reaction (II) was carried out in the presence of sodium hydride, powdered sodium bromide, and DMF.

As demonstrated by Kondo et al., the NaH/DMF approach is generally undesirable for scaled-up production of β-nucleoside analogs because the method does not selectively provide β nucleoside analog product. Rather, a mixture of the α and β anomers of the nucleoside analog product is formed. Thus, β nucleosides synthesized by the NaH/DMF method must be purified from an α:β nucleoside analog mixture. Such a purification step may be particularly difficult if large scale synthesis of nucleoside is desired. In summary, the NaH/DMF method of Kondo et al. does not adequately address the need in the art for an economical method for selectively synthesizing β-nucleosides and β-nucleoside analogs.

As described above, the cited references refer to numerous methods for making β-nucleoside analogs. Each method, while functional in many situations, has drawbacks. Some nucleoside analogs cannot be synthesized by the prior art methods. Often the prior art methods do not provide very good α:β anomeric selectivity. Many of the prior art methods require starting materials that require special synthetic steps and/or are unstable. Accordingly, there is a need in the art for an improved, scalable method for selectively synthesizing the β anomer of nucleosides and nucleoside analogs.

SUMMARY OF THE INVENTION

In one aspect, the present invention provides an improved method for making 2',3'-O-alkylidene β-nucleoside analogs and β-nucleoside analogs. The method generally comprises reacting a 2',3'-alkylidene furanosyl halide with an appropriately protected heterocycle in a nucleophilic polar solvent in the presence of a strong base, to yield a β-2',3'-O-alkylidene nucleoside analog. In a preferred embodiment, the molar ratio of the strong base to the heterocycle is about 1:1 to about 8:1. The 2',3'-O-alkylidene can then be removed to yield the corresponding β-nucleoside analog.

Generally, the 2',3'-O-alkylidene furanosyl halide has the structural formula:

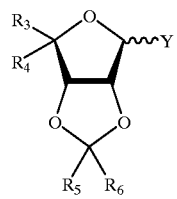

in which:

R$_3$ and R$_4$ are each independently selected from the group consisting of hydrogen, (C$_2$–C$_6$) alkenyl and (CH$_2$)$_n$Q, where n is an integer from 1 to 6;

or R$_3$ and R$_4$ together form a ring of from 3 to 6 carbons, the ring containing 0 to 3 heteroatoms selected from oxygen and nitrogen, and optionally substituted by one or more Q;

R$_5$ and R$_6$ are each independently selected from the group consisting of hydrogen, Q, (C$_1$–C$_6$) alkyl, and (C$_1$–C$_6$) alkyl substituted with one or more Q;

Q is selected from the group consisting of hydrogen, —NO$_2$, —N$_3$, —CN, —SR$_7$, —CX$_3$, —CF$_3$, —X, —OR$_7$, —C(O)OR$_7$, —C(O)R$_7$, —NR$_7$R$_7$, —NH—SO$_2$—R$_7$, and —SO$_2$R$_7$;

X is halogen;

Y is chloro or bromo; and each R$_7$ is independently selected from the group consisting of hydrogen, (C$_1$–C$_6$)alkyl, (C$_2$–C$_6$) alkenyl, (C$_5$–C$_{20}$)aryl, substituted (C$_5$–C$_{20}$)aryl, 5–20 membered heteroaryl substituted 5–20 membered heteroaryl, or R$_7$ is a protecting group.

Preferably, $R_3$ and $R_4$ are hydrogen. The heterocycle is generally any heterocycle having a ring nitrogen capable of forming a covalent bond with the anomeric carbon of a furanose or furanose analog.

In a preferred embodiment the heterocycle has the structural formula:

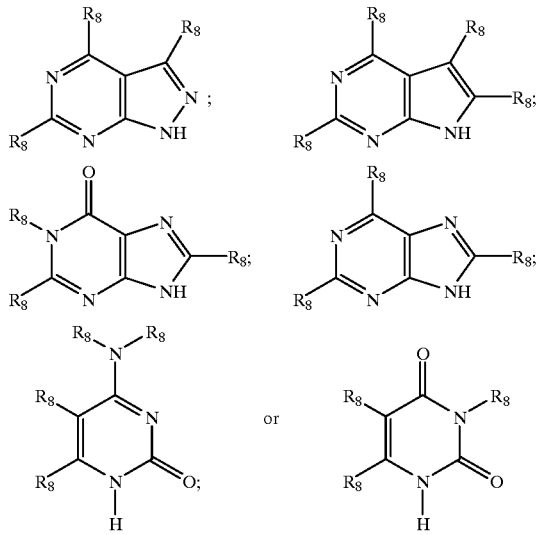

wherein
each $R_8$ is independently selected from the group consisting of Q, $(C_1-C_6)$ alkyl, $(C_1-C_6)$ alkyl substituted with one or more Q, $(C_5-C_{20})$ aryl, $(C_5-C_{20})$ aryl substituted with one or more Q, 5–20 membered heteroaryl, 5–20 membered heteroaryl substituted with one or more Q, $(C_6-C_{26})$ alkaryl, $(C_6-C_{26})$ alkaryl substituted with one or more Q, 6–26 membered alkheteroaryl, and 6–26 membered alkheteroaryl substituted with one or more Q; and Q is as defined previously.

In a preferred embodiment, the strong base is sodium t-butoxide or potassium t-butoxide. In another preferred embodiment, the polar solvent is a nucleophilic polar solvent selected from the group consisting of DMSO, or DMSO mixed with DMF, acetonitrile, tetrahydrofuran or methyl t-butyl ether.

DETAILED DESCRIPTION OF THE INVENTION

As used herein, the following terms shall have the following meanings:

"Alkyl" refers to a saturated straight or branched chain or cyclic hydrocarbon radical. Typical alkyl groups include, but are not limited to, methyl, ethyl, propyl, isopropyl, cyclopropyl, butyl, isobutyl, t-butyl, cyclobutyl, pentyl, isopentyl, cyclopentyl, hexyl, cyclohexyl and the like. In preferred embodiments, the alkyl groups are $(C_1-C_8)$ alkyl, more preferably $(C_1-C_6)$ alkyl, and most preferably $(C_1-C_3)$ alkyl. "Substituted Alkyl" refers to an alkyl radical wherein one or more hydrogen atoms are each independently replaced with another substituent. Typical substituents include, but are not limited to —X, —SR, —CN, —NO$_2$, —NRR, —OR, —CX$_3$, —CF$_3$, —C(O)R, —C(O)OR, —C(O)NRR, —C(NRR)=NR, —C(O)NROR, —C(NRR) =NOR, —NR—C(O)R, —NR—C(O)—NRR, —NR— C(O)—OR, or —NR—SO$_2$—R, where X is halogen and each R is independently selected from the group consisting of —H, —(C$_1$–C$_6$)alkyl, —(C$_2$–C$_6$)alkenyl, —(C$_2$–C$_6$) alkynyl, —(C$_5$–C$_{20}$)aryl, substituted –(C$_5$–C$_{20}$)aryl, 5–20 membered heteroaryl, substituted 5–20 membered heteroaryl, —(C$_6$–C$_{26}$)alkaryl, substituted —(C$_6$–C$_{26}$) alkaryl, 6–26 membered alkheteroaryl, and substituted 6–26 membered alkheteroaryl, as defined herein.

"Alkenyl" refers to an unsaturated straight or branched chain or cyclic hydrocarbon radical having at least one carbon-carbon double bond. The radical may be in either the cis or trans conformation about the double bond(s). Typical alkenyl groups include, but are not limited to, ethenyl, vinylidene, propenyl, propylidene, isopropenyl, isopropylidene, butenyl, butenylidene, isobutenyl, tert-butenyl, cyclobutenyl, pentenyl, isopentenyl, cyclopentenyl, hexenyl, cyclohexenyl and the like. In preferred embodiments, the alkenyl group is (C$_2$–C$_8$) alkenyl, more preferably (C$_2$–C$_6$) alkenyl, and most preferably (C$_2$–C$_3$) alkenyl.

"Substituted Alkenyl" refers to an alkenyl radical wherein one or more hydrogen atoms are each independently replaced with another substituent. Typical substituents include, but are not limited to —X, —SR, —CN, —NO$_2$, —NRR, —OR, —CX$_3$, —CF$_3$, —C(O)R, —C(O)OR, —C(O)NRR, —C(NRR)=NR, —C(O)NROR, —C(NRR) =NOR, —NR—C(O)R, —NR—C(O)—NRR, —NR— C(O)—OR, or —NR—SO$_2$—R, where X is halogen and each R is independently selected from the group consisting of —H, —(C$_1$–C$_6$)alkyl, —(C$_2$–C$_6$)alkenyl, —(C$_2$–C$_6$) alkynyl, —(C$_5$–C$_{20}$)aryl, substituted —(C$_5$–C$_{20}$)aryl, 5–20 membered heteroaryl, substituted 5–20 membered heteroaryl, —(C$_6$–C$_{26}$) alkaryl, substituted —(C$_6$–C$_{26}$) alkaryl, 6–26 membered alkheteroaryl, and substituted 6–26 membered alkheteroaryl, as defined herein.

"Alkynyl" refers to an unsaturated straight or branched chain or cyclic hydrocarbon radical having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is (C$_2$–C$_8$) alkynyl, more preferably (C$_2$–C$_6$), and most preferably (C$_2$–C$_3$) alkynyl.

"Substituted Alkynyl" refers to an alkynyl radical wherein one or more hydrogen atoms are each independently replaced with another substituent. Typical substituents include, but are not limited to —X, —SR, —CN, —NO$_2$, —NRR, —OR, —CX$_3$, —CF$_3$, —C(O)R, —C(O)OR, —C(O)NRR, —C(NRR)=NR, —C(O)NROR, —C(NRR) =NOR, —NR—C(O)R, —NR—C(O)—NRR, —NR—C (O)—OR, or —NR—SO$_2$—R, where X is halogen and each R is independently selected from the group consisting of —H, —(C$_1$–C$_6$)alkyl, —(C$_2$–C$_6$)alkenyl, —(C$_2$–C$_6$) alkynyl, —(C$_5$–C$_{20}$)aryl, substitute —(C$_5$–C$_{20}$)aryl, 5–20 membered heteroaryl, substituted 5–20 membered heteroaryl, —(C$_6$–C$_{26}$)alkaryl, substituted (C$_6$–C$_{26}$)alkaryl, 6-26 membered alkheteroaryl, and substituted 6–26 membered alkaryl as defined herein.

"Aryl" refers to an unsaturated cyclic hydrocarbon radical having a conjugated π electron system. Typical aryl groups include, but are not limited to, penta-2,4-dienyl, phenyl, naphthyl, aceanthrylyl, acenaphthyl, anthracyl, azulenyl, chrysenyl, indacenyl, indanyl, ovalenyl, perylenyl, phenanthrenyl, phenalenyl, picenyl, pyrenyl, pyranthrenyl, rubicenyl and the like. In preferred embodiments, the aryl group is (C$_5$–C$_{20}$) aryl, more preferably (C$_5$–C$_{10}$) aryl, and most preferably phenyl.

"Substituted Aryl" refers to an aryl radical wherein one or more hydrogen atoms are each independently replaced with another substituent. Typical substituents include, but are not limited to —X, —SR, —CN, —NO$_2$, —NRR, —OR, —CX$_3$, —CF$_3$, —C(O)R, —C(O)OR, —C(O)NRR, —C(NRR)=NR, —C(O)NROR, —C(NRR)=NOR, —NR—C(O)R, —NR—C(O)—NRR, —NR—C(O)—OR, or —NR—SO$_2$—R, where X is halogen and each R is independently selected from the group consisting of —H, —(C$_1$–C$_6$)alkyl, —(C$_2$–C$_6$)alkenyl, —(C$_2$–C$_6$)alkynyl, —(C$_5$–C$_{20}$)aryl, substituted —(C$_5$–C$_{20}$)aryl, 5–20 membered heteroaryl, substituted 5–20 membered heteroaryl, —(C$_6$–C$_{26}$)alkaryl, substituted (C$_6$–C$_{26}$)alkaryl, 6–26 membered alkheteroaryl, and substituted 6–26 membered alkaryl as defined herein.

"Alkaryl" refers to a straight-chain alkyl, alkenyl or alkynyl group wherein one of the hydrogen atoms bonded to the terminal carbon is replaced with an aryl moiety. Alkaryl also refers to a branched-chain alkyl, alkenyl or alkynyl group wherein one of the hydrogen atoms bonded to a terminal carbon is replaced with an aryl moiety. Typical alkaryl groups include, but are not limited to, benzyl, benzylidene, benzylidyne, benzenobenzyl, naphthalenobenzyl and the like. In preferred embodiments, the alkaryl group is (C$_6$–C$_{26}$) alkaryl, i.e., the alkyl, alkenyl or alkynyl moiety of the alkaryl group is (C$_1$–C$_6$) and the aryl moiety is (C$_5$–C$_{20}$). In particularly preferred embodiments the alkaryl group is (C$_6$–C$_{13}$), i.e., the alkyl, alkenyl or alkynyl moiety of the alkaryl group is (C$_1$–C$_3$) and the aryl moiety is (C$_5$–C$_{10}$).

"Substituted Alkaryl" refers to an alkaryl radical wherein one or more hydrogen atoms on the aryl moiety are each independently replaced with another substituent. Typical substituents include, but are not limited to —X, —SR, —CN, —NO$_2$, —NRR, —OR, —CX$_3$, —CF$_3$, —C(O)R, —C(O)OR, —C(O)NRR, —C(NRR)=NR, —C(O)NROR, —C(NRR)=NOR, —NR—C(O)R, —NR—C(O)—NRR, —NR—C(O)—OR, or —NR—SO$_2$—R, where X is halogen and each R is independently selected from the group consisting of —H, —(C$_1$–C$_6$)alkyl, —(C$_2$–C$_6$)alkenyl, —(C$_2$–C$_6$)alkynyl, —(C$_5$–C$_{20}$)aryl, substituted —(C$_5$–C$_{20}$) aryl, 5–20 membered heteroaryl, substituted 5–20 membered heteroaryl, —(C$_6$–C$_{26}$)alkaryl, substituted —(C$_6$–C$_{26}$)alkaryl, 6–26 membered -alkheteroaryl, and substituted 6–26 membered -alkheteroaryl, as defined herein.

"Heteroaryl" refers to an aryl moiety wherein one or more carbon atoms has been replaced with another atom, such as N, P, O, S, As, Ge, Se, Si, Te, etc. Typical heteroaryl groups include, but are not limited to, acridarsine, acridine, arsanthridine, arsindole, arsindoline, benzodioxole, benzothiadiazole, carbazole, β-carboline, chromane, chromene, cinnoline, furan, imidazole, indazole, indole, (1,3)-benzodioxole, oxindole, azaindole, isoindole, indolizine, isoarsindole, isoarsinoline, isobenzofuran, isochromane, isochromene, isoindole, isophosphoindole, isophosphinoline, isoquinoline, isothiazole, isoxazole, naphthyridine, perimidine, phenanthridine, phenanthroline, phenazine, phosphoindole, phosphinoline, phthalazine, piazthiole, pteridine, purine, pyran, pyrazine, pyrazole, pyridazine, pyridine, pyrimidine, pyrrole, pyrrolizine, quinazoline, quinoline, quinolizine, quinoxaline, selenophene, tellurophene, thiazopyrrolizine, thiophene and xanthene. In preferred embodiments, the heteroaryl group is a 5–20 membered heteroaryl, with 5–10 membered heteroaryl being particularly preferred.

"Substituted Heteroaryl" refers to a heteroaryl radical wherein one or more hydrogen atoms are each independently replaced with another substituent. Typical substituents include, but are not limited to —X, —SR, —CN, —NO$_2$, —NRR, —OR, —CX$_3$, —CF$_3$, —C(O)R, —C(O)OR, —C(O)NRR, —C(NRR)=NR, —C(O)NROR, —C(NRR)=NOR, —NR—C(O)R, —NR—C(O)—NRR, —NR—C(O)—OR, or —NR—SO$_2$—R, where X is halogen and each R is independently selected from the group consisting of —H, —(C$_1$–C$_6$)alkyl, —(C$_2$–C$_6$)alkenyl, —(C$_2$–C$_6$)alkynyl, —(C$_5$–C$_{20}$)aryl, substituted (C$_5$–C$_{20}$) aryl, 5–20 membered -heteroaryl, substituted 5–20 membered -heteroaryl, —(C$_6$–C$_{26}$) alkaryl, substituted —(C$_6$–C$_{26}$)alkaryl, 6–26 membered -alkheteroaryl, and substituted 6–26 membered -alkheteroaryl, as defined herein.

"Alkheteroaryl" refers to a straight or branched chain alkyl, alkenyl or alkynyl group where one of the hydrogen atoms bonded to a terminal carbon atom is replaced with a heteroaryl moiety. In preferred embodiments, the alkheteroaryl group is a 6–26 membered alkheteroaryl, i.e., the alkyl, alkenyl or alkynyl moiety of the alkheteroaryl is (C$_1$–C$_6$) and the heteroaryl moiety is a 5–20-membered heteroaryl. In particularly preferred embodiments, the alkheteroaryl is a 6–13 membered alkheteroaryl, i.e., the alkyl, alkenyl or alkynyl moiety is (C$_1$–C$_3$) and the heteroaryl moiety is a 5–10 membered heteroaryl.

"Substituted alkheteroaryl" refers to an alkheteroaryl radical wherein one or more hydrogens on the heteroaryl moiety are each independently replaced with another substituent. Typical substituents include, but are not limited to —X, —SR, —CN, —NO$_2$, —NRR, —OR, —CX$_3$, —CF$_3$, —C(O)R, —C(O)OR, —C(O)NRR, —C(NRR)=NR, —C(O)NROR, —C(NRR)=NOR, —NR—C(O)R, —NR—C(O)—NRR, —NR—C(O)—OR, or —NR—SO$_2$—R, where X is halogen and each R is independently selected from the group consisting of —H, —(C$_1$–C$_6$)alkyl, —(C$_2$–C$_6$)alkenyl, —(C$_2$–C$_6$) alkynyl, —(C$_5$–C$_{20}$)aryl, substituted —(C$_5$–C$_{20}$)aryl, 5–20 membered -heteroaryl, substituted 5–20 membered -heteroaryl, —(C$_6$–C$_{26}$)alkaryl, substituted —(C$_6$–C$_{26}$)alkaryl, 6–26 membered -alkheteroaryl, and substituted 6–26 membered -alkaryl as defined herein.

"Hydroxyl protecting group" includes, but is not limited to, a group that converts an hydroxyl to an ether or ester. Representative ethers formed by hydroxyl protecting groups include methyl ether, methoxymethyl ether, methylthiomethyl ether, 2-methoxyethoxymethyl ether, bis(2-chloroethoxy)methyl ether, tetrahydropyranyl ether, tetrahydrothiopyranyl ether, 4-methoxytetrahydropyranyl ether, 4-methoxytetrahydro-thiopyranyl ether, tetrahydrofuranyl ether, tetrahydrothiofuranyl ether, 1-ethoxyethyl ether, 1-methyl-1-methoxyethyl ether, 2-(phenylselenyl)ethyl ether, t-butyl ether, allyl ether, benzyl ether, o-nitrobenzyl ether, triphenylmethyl ether, α-napthyldiphenylmethyl ether, p-methoxyphenyl-diphenylmethyl ether, 9-(9-phenyl-10-oxo)anthryl ether, trimethylsilyl ether, isopropyldimethylsilyl ether, t-butyldimethylsilyl ether, t-butyldiphenylsilyl ether, tribenzylsilyl ether, triisopropylsilyl ether, p-methoxybenzyl ether, 3,4 dimethoxybenzyl ether, o-nitrobenzyl ether, p-nitrobenzyl ether, p-halobenzyl ether, 2,6-dichlorobenzyl ether, p-cyanobenzyl ether, p-phenylbenzyl ether, 2-and 4-picolyl ether, 3-methyl-2-picolyl N-oxido ether, diphenylmethyl ether, triphenylmethyl ether, triphenylmethyl derivative ethers, p-methoxyphenyldiphenylmethyl ether, di(p-methoxyphenyl) ether, phenylmethyl ether, tri(p-methoxyphenyl) methyl ether, 9-anthryl ether, 9-(9-phenyl) xanthenyl ether, 9-(9-phenyl-10-oxo)anthryl ether, 1,3-benzodithiolan-2-yl ether, benzisothiazolyl S,S-dioxido ether, trimethylsilyl ether, triethylsilyl ether, triisopropylsilyl ether, dimethylisopropylsilyl ether, diethylisopropylsilyl ether, dimethylhexylsilyl ether, t-butyldimethylsilyl ether, t-butyldiphenylsilyl ether, tribenzylsilyl ether, tri-p-xylylsilyl ether, triphenylsilyl ether, diphenylmethylsilyl ether, and t-butylmethoxyphenylsilyl ether. Representative esters formed by hydroxyl protecting groups include acetate ester, trichloroacetate ester, phenoxyacetate ester, isobutyrate ester, pivaloate ester, adamantoate ester, benzoate ester, 2,4,5-trimethylbenzoate ester, carbonate esters, N-phenylcarbamate ester, nitrate ester, and 2,4-dinitrophenylsulfenate ester. See, e.g., Greene & Wuts, *Protective Groups in Organic Synthesis,* 1991, John Wiley & Sons, New York.

"Halogen" as used herein, unless otherwise indicated, includes chloro, fluoro, bromo and iodo.

The present invention provides an improved process for coupling sugars to heterocycles to stereoselectively form β-nucleosides and/or β-nucleoside analogs. In the method of the present invention, β-nucleosides or β-nucleoside analogs are selectively synthesized by coupling a heterocycle with a furanosyl halide in a nucleophilic polar solvent in the presence of a strong base. The coupling reaction of the present invention is advantageous because there is no requirement for α-furanosyl halide, and the reaction results in the formation of nucleosides and nucleoside analogs with high β selectivity. Because the reagents used in the methods of the present invention are stable, and heavy metals are not used, the method can be conveniently scaled-up to provide the β-nucleoside analogs of interest in kilogram quantities.

The method of the present invention is represented by reaction scheme (III):

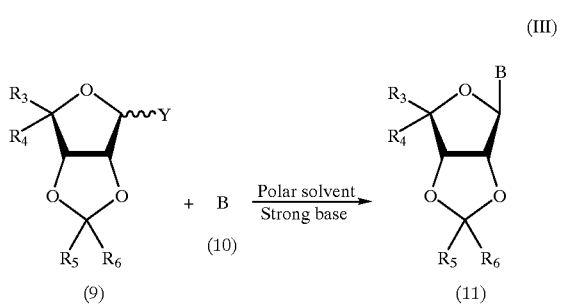

wherein:
- $R_3$ and $R_4$ are each independently selected from the group consisting of hydrogen, $(C_2–C_6)$ alkenyl and $(CH_2)_nQ$, where n is an integer from 1 to 6,
- or $R_3$ and $R_4$ together form a ring of from 3 to 6 carbons, the ring containing 0 to 3 heteroatoms selected from oxygen and nitrogen, and optionally substituted by one or more Q;
- $R_5$ and $R_6$ are each independently selected from the group consisting of hydrogen, Q, $(C_1–C_6)$ alkyl, and $(C_1–C_6)$ alkyl substituted with one or more Q;
- Q is selected from the group consisting of hydrogen, —$NO_2$, —$N_3$, —CN, —$SR_7$, —$CX_3$, —$CF_3$, —X, —$OR_7$, —$C(O)OR_7$, —$C(O)R_7$, —$NR_7R_7$, —NH—$SO_2$—$R_7$, and —$SO_2R_7$;
- each $R_7$ is independently selected from the group consisting of hydrogen, $(C_1–C_6)$alkyl, $(C_2–C_6)$ alkenyl, $(C_5–C_{20})$aryl, substituted $(C_5–C_{20})$aryl, 5–20 membered heteroaryl, and substituted 5–20 membered heteroaryl, or $R_7$ is a protecting group;
- X is halogen;
- Y is chloro or bromo; and
- B is a heterocycle having a ring nitrogen capable of forming a covalent bond with the anomeric carbon of a furanose or furanose analog.

In a preferred embodiment, $R_3$ and $R_4$ are each hydrogen.

In a further preferred embodiment, $R_3$ is —$CH_2OR_7$ and $R_4$ is H, or $R_3$ is H and $R_4$ is —$CH_2OR_7$, where $R_7$ is a protecting group.

In a further preferred embodiment, $R_5$ and $R_6$ are each methyl.

In a further preferred embodiment, the 2',3'-O-alkylidene furanosyl halide is 2,3-O-isopropylidine-β-D-erythrofuranosyl chloride.

The furanosyl halide (9) may be a mixture of α/β furanosyl halide or pure β-furanosyl halide. Thus, reaction (III) does not require any α-furanosyl halide. Without being bound to any particular theory, it is believed that if a mixture of α/β furanosyl halide (9) is used, the α-anomer converts to the β-anomer prior to reacting with the heteroanion in reaction (III). Regardless of whether an α/β furanosyl halide mixture, α-furanosyl halide or β-furanosyl halide is used in reaction (III), the heteroanion base (B) will be trans with respect to the 2',3'-O-alkylidene in compounds (11) synthesized using reaction (III).

The 2',3'-O-alkylidene, β-nucleoside analogs (11) can be deprotected to form the corresponding β-nucleoside analogs by conventional means. For example, they may be deprotected by dissolving the 2',3'-O-alkylidene β-nucleoside analogs (11) in a hydroxylic solvent in the presence of an acid according to reaction scheme (IV) and as further detailed infra and in the Examples.

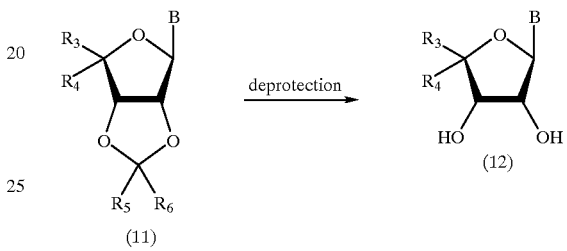

Other suitable deprotection methods are known in the art. See e.g. Greene and Wuts, *Protective Groups in Organic Synthesis*, 1991, John Wiley & Sons, New York.

As used herein, the numbering system of the furanosyl ring is conventional and is as follows:

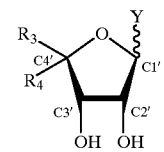

where C1' is defined as the anomeric carbon. Thus, the terms "β-nucleoside" and "β-nucleoside analog" as used herein refer to compounds of formula (12) in which the stereochemistry of the C1' anomeric carbon is β. Additionally, the terms "2',3'-O-alkylidene β-nucleoside" and "2',3'-O-alkylidene β-nucleoside analog" as used herein refer to compounds of formula (12) in which the stereochemistry of the C1' anomeric carbon is β. Furthermore, all "nucleoside analogs" referred to herein include "nucleosides", and all "2',3'-O-alkylidene β-nucleoside analogs" referred to herein include "2',3'-O-alkylidene β-nucleosides".

Heterocycles within the scope of the present invention include all heterocycles used in the synthesis of nucleosides or nucleoside analogs. All such heterocycles contain a ring NH that is capable of forming a covalent bond to the anomeric C1' carbon of furanose (9). This ring NH is referred to herein as the "candidate NH". Heterocycles of the present invention therefore include, but are not limited to, pyrimidines such as cytosine, thymine, and uracil, purines such as adenine, guanine, caffeine, and theobromine, pyrrolopyrimidines, pyrrolopyrimidine-4-ones, pyrazolopyrimidines, and 3-haloallopurinols. See, e.g., U.S. Pat. No. 5,674,998; Ramasay et al., supra, Kondo et al., supra, and Cottam et al., supra. Other examples of heterocycles within the scope of the present invention are described in Fasman, 1980, *Biochemistry and Molecular*

Biology, CRC Press. Additionally, U.S. Pat. Nos. 5,852,027, 5,840,743, 5,837,871, 5,830,881, 5,808,147, 5,763,596, 5,747,473, 5,744,596, 5,726,174, 5,693,771, 5,605,903, 5,246,931, 5,110,926, 4,859,677, and 4,751,292 provide several examples of representative nucleoside analogs, and their corresponding heterocycles, which are within the scope of the present invention.

Generally, heterocycles in which the candidate NH is in a five membered aromatic ring are preferred. Accordingly, heterocycles such as pyrrolopyrimidines, pyrrolopyrimidine-4-ones, pyrazolopyrimidines, and purines are preferred. More preferably, the heterocycle is a pyrrolo(2,3-d)pyrimidine, pyrrolo(2,3-d)pyrimidine-4-one, or pyrazolo(3,4-d)pyrimidine.

In a preferred embodiment, the heterocycle has the structural formula:

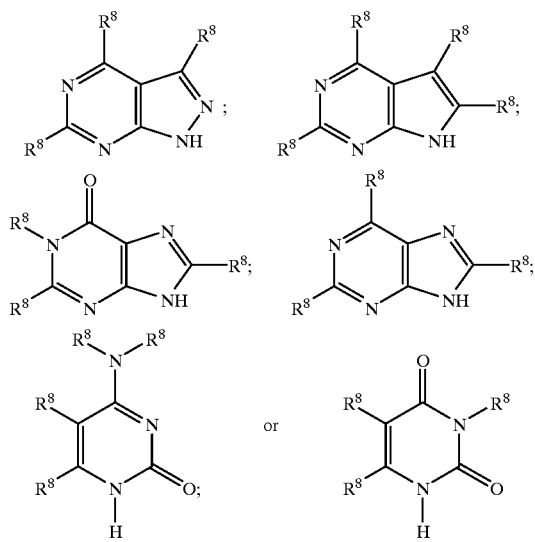

wherein each $R_8$ is independently selected from the group consisting of Q, $(C_1-C_6)$alkyl, $(C_1-C_6)$ alkyl substituted with one or more Q, $(C_5-C_{20})$aryl, $(C_5-C_{20})$aryl substituted with one or more Q, 5–20 membered heteroaryl, 5–20 membered heteroaryl substituted with one or more Q, $(C_6-C_{26})$alkaryl, $(C_6-C_{26})$alkaryl substituted with one or more Q, 6–26 membered alkheteroaryl, and 6–26 membered alkheteroaryl substituted with one or more Q; and Q is as defined previously.

In another preferred embodiment, the heterocycle has the structural formula:

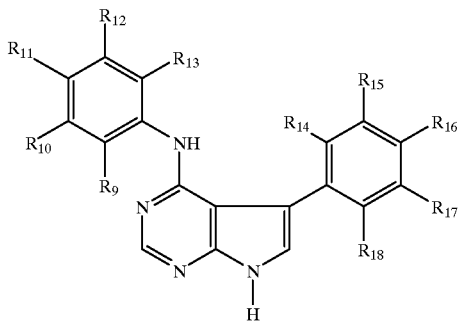

wherein:
$R_9$, $R_{10}$, $R_{11}$, $R_{12}$, $R_{13}$, $R_{14}$, $R_{15}$, $R_{16}$, $R_{17}$, and $R_{18}$, are each independently selected from the group consisting of Q, $(C_1-C_6)$alkyl, $(C_1-C_6)$alkyl substituted with one or more Q, $(C_5-C_{20})$ aryl, $(C_5-C_{20})$aryl substituted with one or more Q, 5–20 membered heteroaryl, 5–20 membered heteroaryl substituted with one or more Q, $(C_6-C_{26})$alkaryl, $(C_6-C_{26})$alkaryl substituted with one or more Q, 6–26 membered alkheteroaryl, and 6–26 membered alkheteroaryl substituted with one or more Q; and Q is as defined previously.

In a preferred embodiment, $R_9$, $R_{10}$, $R_{11}$, $R_{12}$, and $R_{13}$ are each independently selected from the group consisting of hydrogen, halogen, $-NH_2$, $-NO_2$, $-CN$, $-CF_3$ and $-OCH_3$; and $R_{14}$, $R_{15}$, $R_{16}$, $R_{17}$, and $R_{18}$ are each hydrogen.

In a further preferred embodiment $R_{11}$ is fluoro and $R_9$, $R_{10}$, $R_{12}$ and $R_{13}$ are each hydrogen.

In a further preferred embodiment, the heterocycle is 5-phenyl-4-N-(4-fluorophenyl)aminopyrrolo(2,3-d) pyrimidine.

Some heterocycles and sugars of the present invention require the addition of one or more protecting groups prior to coupling reaction (III). For example, amide oxygens and hydroxyl groups may require protection. Suitable protecting groups are those that are resistant to cleavage under the strong basic conditions of coupling reaction (III).

In sugars of the present invention, an alkylidene is used to protect C2' and C3' hydroxyls by forming an ether of both hydroxyls. Other hydroxyls present in the sugar or heterocycle may be protected by conventional means including converting the hydroxyls to ethers or esters using standard hydroxyl protecting groups. The actual protecting group used to protect particular hydroxyls is highly dependent upon the exact nature of the sugar and heterocycle that are to be coupled. If a hydroxyl is protected by converting it to an ether or an ester, there are several different types of ethers or esters that may be formed. See, e.g., the definition of "hydroxyl protecting group" provided supra, or Greene & Wuts, *Protective Groups in Organic Synthesis,* supra.

The method used to protect amides is highly dependent upon the exact nature of the heterocycle and sugar to be coupled. Amides may be protected by N or O alkylation. In some cases, conventional amide protecting groups including, but not limited to, silyl groups, phosphinothioyl, 2-nitrophenyl, cyanoethyl or nitrophenylethyl groups may be used. See e.g. Daskalov et al., 1981, *Bull. Chem. Soc. Japan,* 54, 3076; Jones et al, 1981, *Tetrahedron Lett.,* 22, 4755; Gaffney and Jones, 1982, *Tetrahedron Lett.,* 23, 2257; Trichtinger et al., 1983, *Tetrahedron Lett.,* 24, 211.

Depending upon the substituents attached to the heterocycle and the exact functionality of $R_3$ and $R_4$ of the sugar, additional protecting groups may be necessary. Such protecting groups are well known in the art. For example, an extensive selection of base stable protecting groups is found in Greene and Wuts, *Protective Groups in Organic Synthesis,* John Wiley & Sons, New York.

Once coupling reaction (III) is complete, the protecting groups are removed. The alkylidene group that protects the furanosyl C2' and C3' hydroxyls during reaction (III) is removed under acidic conditions in the presence of a hydroxylic solvent. Suitable acids for this deprotection step include any acid that is strong enough to catalyze the removal of the alkylidene group, including, but not limited to, HCl, sulfuric acid, or trifluoroacetic acid. Suitable hydroxylic solvents include alcohols and $H_2O$.

Ether linked hydroxyl protecting groups may be removed using mildly acidic conditions to yield the free hydroxyl. See, e.g., Gait, 1984, *Oligonucleotide Synthesis,* supra. Acyl protected exocyclic amines are typically deacylated by the addition of concentrated ammonia. See e.g. Gait, 1984, *Oligonucleotide Synthesis,* supra. Alternative deprotection methods are known to those of skill in the art. Representative deprotection methods are found in Greene and Wuts, *Protective Groups in Organic Synthesis*, supra.

The C2' and C3' carbons of the furanosyl halide are linked by an alkylidene to form a five membered ring according to structural formula (9):

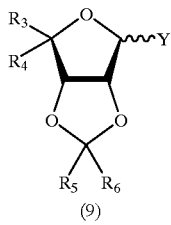

(9)

wherein $R_3$, $R_4$, $R_5$, $R_6$ and Y are as previously defined.

In a preferred embodiment, $R_5$ and $R_6$ are methyl and the alkylidene is therefore isopropylidene.

Reaction scheme (III) is not dependent on the absolute stereochemistry of the five membered ring of formula (9). One of skill in the art will recognize that the carbon atom to which $R_5$ and $R_6$ are attached is a chiral center if $R_5$ and $R_6$ are different. Reaction scheme (III) is not dependent upon the chirality of this center. Further, the chirality of this center is preserved during reaction scheme (III) and, consequently, the stereochemistry of this chiral center will be preserved in the corresponding β-2',3'-O-alkylidene nucleoside analog (11).

In order to effect the anomer specific reaction depicted in scheme (III), nucleophilic polar solvents should be used. Without intending to be limited to any particular theory, it is believed that the nucleophilic polar solvent is required because it is involved in the reaction mechanism of reaction scheme (III). Suitable nucleophilic polar solvents include any that allow dissolution of the heterocycle, sugar substrates and the strong base, including but not limited to N,N-dimethylformamide (DMF), acetonitrile, tetrahydrofuran (THF), dimethylsulfoxide (DMSO), and mixtures thereof. In a preferred embodiment, such a mixture is a DMSO:solvent mixture.

Unexpectedly, it has been found that DMSO and DMSO:solvent mixtures work much better than other nucleophilic polar solvents. Thus, the nucleophilic polar solvent is preferably DMSO or a DMSO:solvent mixture. The use of a DMSO:solvent mixture rather than DMSO results in no measurable improvement in the α:β selectivity of the reaction. However the use of a DMSO:solvent mixture rather than DMSO may, depending on the substrates used, improve the efficiency of reaction (III). If a DMSO:solvent mixture is used, it is preferable that DMF, acetonitrile, THF, and/or methyl t-butyl ether (MTBE) be used to formulate the DMSO:solvent mixture. It is expected that any proportion of DMSO relative to solvent may be used to formulate the DMSO:solvent mixture as long as an appreciable amount of DMSO, i.e., at least about 15% DMSO (by volume) to total volume, such as, e.g., from about 15% to about 25% DMSO (by volume), is present in the DMSO:solvent mixture. Such a DMSO:solvent mixture may comprise 1 part DMSO mixed with 0 to 3 parts of a solution comprising one or more solvents selected from the group consisting of DMF, acetonitrile, THF and MTBE. Thus, e.g., a DMSO:solvent mixture consisting of 1 part DMSO to 3 parts MTBE was adequate to support reaction scheme (III). TABLE 1 details some illustrative nucleophilic polar solvents of the present invention.

TABLE 1

Examples of Suitable Nucleophilic
Polar Solvents For Reaction Scheme (III)

Solvent

100% DMSO
100% DMF
100% acetonitrile
100% THF
1:1 DMSO:acetonitrile
1:1 DMSO:THF
1:1 DMSO:MTBE
1:3 DMSO:MTBE Trace amounts of water are tolerated in reaction scheme (III). However, it has been found that the presence of one part water to two parts sugar substrate substantially impairs the coupling reaction. Thus, the polar nucleophilic solvents are preferably anhydrous, and the reaction is preferably carried out under anhydrous conditions, especially when hygroscopic solvents are used. Because anhydrous conditions are preferred, the reaction is preferably performed in an inert atmosphere such as helium, nitrogen, or argon.

In a preferred embodiment, the method of the present invention is carried out where the 2',3'-O-alkylidene furanosyl halide is 2,3-O-isopropylidene-β-D-erythrofuranosyl chloride; the appropriately protected heterocycle is 5-phenyl-4-N-(4-fluorophenyl)aminopyrrolo(2,3-d) pyrimidine; and the nucleophilic polar solvent is DMSO.

The coupling of the 2',3'-O-alkylidene furanosyl halide with the heterocycle is carried out in the presence of a strong base. The strong base causes the anionization of ring nitrogens that are capable of forming anions. The furanosyl halide reacts with the anionized ring nitrogen, resulting in the alkylation of the ring nitrogen by the furanosyl. If there is only one anionized ring nitrogen in the heterocycle, only one alkylated heterocyle will form. If the heterocycle contains two ring nitrogens that are capable of being anionized by the strong base, a mixture of heterocycle anion in which some of the heterocycle is anionized at the first ring nitrogen and some of the heterocycle is anionized at the second ring nitrogen, will form. Such a mixture of heterocyle anion will result in a corresponding mixture of alkylated heterocycle products. If the heterocycle contains more than two ring amines, more complex mixtures of alkylated heterocycle products could form. Because each alkylated product in the mixture represents the coupling of the sugar to a different nitrogen on the heterocycle, the alkylated products will have distinctive chemical properties. Therefore, even if undesired alkylated-heterocycle forms, it can typically be separated out from the desired nucleoside analog using conventional purification methods such as acid extraction. However, it is desirable to minimize the undesired alkylated products in order to conserve the furanosyl halide and heterocycle starting reagents.

The formation of undesired alkylated heterocycle products is minimized by optimizing the amount of heterocycle that forms an anion at the desired nitrogen in the heterocycle. For example, when 5-phenyl-4-N-(4-fluorophenyl) aminopyrrolo(2,3-d)pyrimidine is mixed with a strong base, an anion forms that resonates between the one and seven ring nitrogen. Alkylation of the seven nitrogen (N7-alkylation) generates the desired nucleoside whereas alkylation of the one nitrogen (N1-alkylation) results in an undesired side product. It has been unexpectedly discovered that, by using sodium t-butoxide or potassium t-butoxide, the amount of N7-alkylation relative to N1-alkylation may be optimized. Accordingly, as described in Example 2 below, a 3:1 mixture of N7- to N1- alkylated heterocycle may be generated using sodium t-butoxide. Because the N1-alkylated heterocycle is more basic than the N7-alkylated heterocycle, the N1-alkylated heterocycle is easily removed from the N7:N1 alkylated heterocycle mixture by acid extraction.

Any strong base that is capable of forming the anion of a heterocycle containing a ring NH is within the scope of the invention. Suitable bases generally include alkaline hydroxides such as sodium hydroxide or potassium hydroxide, ($C_4$–$C_{10}$) alkaline alkoxides such as alkaline t-butoxide and alkaline t-pentoxide (alkaline amylate), as well as alkaline hydrides. In some instances, an alkaline earth hydroxide such as $Mg(OH)_2$ or $Ca(OH)_2$ may drive reaction scheme (III) to a limited extent. However, it is expected that alkaline earth bases will generally not work very well. While the strong bases of the present invention are generally alkali metal bases, it is expected that, of the alkalis, lithium will work very poorly because of its physical properties. Preferably the strong base is an alkaline hydride or alkaline t-butoxide. More preferably, the strong base is sodium hydride, potassium hydride, sodium t-butoxide, sodium t-pentoxide, potassium t-butoxide, or potassium t-pentoxide. More preferably, the strong base is sodium t-butoxide or potassium t-butoxide. Most preferably, the strong base is sodium t-butoxide.

Kondo et al., supra, teach a method for synthesizing nucleoside analogs that uses the strong base, sodium hydride, and the nucleophilic polar solvent, DMF. However, Kondo et al. failed to synthesize nucleosides that had a low α:β ratio. To address this selectivity problem, Kondo et al. attempted to use a variety of salts as additives. However, even after numerous attempts to improve anomeric selectivity, they were only able to achieve an α:β ratio of nucleoside product of 1:2 using their sodium hydride/DMF approach. The methods of the present invention provide much better (i.e., lower) α:β ratios of nucleoside product than Kondo et al. In the case of the synthesis of 4-N-(4-fluorophenyl)amino-5-phenyl-1-(β-D-erythrofuranosyl) pyrrolo-(2,3-d)pyrimidine (the title compound of Example 4 below) using DMSO and sodium t-butoxide, the α:β ratio of nucleoside product was less than 1:100. Depending upon the specific sugar and heteroanion substrate used, the methods of the present invention may provide even better α:β ratios of nucleoside product. However, depending upon the specific sugar and heteroanion substrate used, the methods of the present invention will generally provide an α:β ratio of nucleoside product of less than 1:2, more typically less than 1:50 and frequently less than 1:100 or better. The methods of the present invention demonstrate that the combination of sodium hydride and DMF used by Kondo et al. is not adequate. Generally, the methods of the present invention will produce better (i.e., lower) α:β ratio of nucleoside product than Kondo et al. regardless of the sugar and heteroanion substrate used.

Usually, the molar ratio of strong base to heterocycle is in the range of about 1:1 to about 8:1. It has been determined that a molar ratio of strong base to heterocycle of at least about 1:1 is necessary to efficiently drive reaction (III). Usage of less than about a 1:1 molar ratio of strong base to heterocycle will result in the formation of some nucleoside analog. However, the reaction (III) will prematurely end and result in the waste of substantial amount of reagents. To prevent this, a molar ratio of strong base relative to heterocycle of about 2:1 to 4:1 is typically used.

Reaction scheme (III) has been conducted generally at room temperatures (about 20° C. to about 30° C.). Elevated temperatures such as about 40° C. to about 50° C. have been found to have no beneficial impact on either the yield of reaction (III) or the α:β ratio of the nucleoside or nucleoside analog product.

Reaction (III) is not dependent on the molar ratio of 2',3'-O-alkylidene furanosyl halide to heterocycle. A molar ratio of 2',3'-O-alkylidene furanosyl halide to heterocycle of about 1:1 to about 3:1 can be used, and a molar ration of 3:2 to 2:1 is typically used. Preferably the molar ratio of 2',3'-O-alkylidene furanosyl halide to heterocycle is about 3:2.

Reaction (III) can be scaled up without loss of yield. For example, reaction (III) has been successfully completed using gram quantities (Example 2 below) and kilogram quantities (Example 3 below) of 2',3'-O-alkylidene furanosyl halide and heterocycle. The α:β ratio of nucleoside analogs produced using the methods of the present invention is generally significantly better (i.e., less) than those produced by prior art reactions. For example, in Example 2, the α:β ratio was less than 1:100. This ratio is a conservative estimate because high performance liquid chromatography (HPLC) of the final product was unable to detect any α-nucleoside product. In fact, the α:β ratio may be significantly less than 1:100.

The length of time necessary to complete reaction (III) is dependent upon the strong base and the specific 2',3'-O-alkylidene furanosyl halide and heterocycle that are used. However, it is generally appreciated that reaction (III) will be complete in about two hours. In the case of 4-N-(4-fluorophenyl)amino-5-phenyl-1-(2,3-O-isopropylidene-β-D-erythrofuran-osyl)pyrrolo-(2,3-d)pyrimidine, reaction times on the order of 14 to 15 hours have been found to provide no improvement in the amount of yield relative to a two hour reaction time. The reaction is monitored by checking for the disappearance of starting materials in samples of the reaction by HPLC.

In a further embodiment, the present invention provides a method for synthesizing ribopurines and ribopyrimidines. In this embodiment, ribopurines are synthesized according to formula (V):

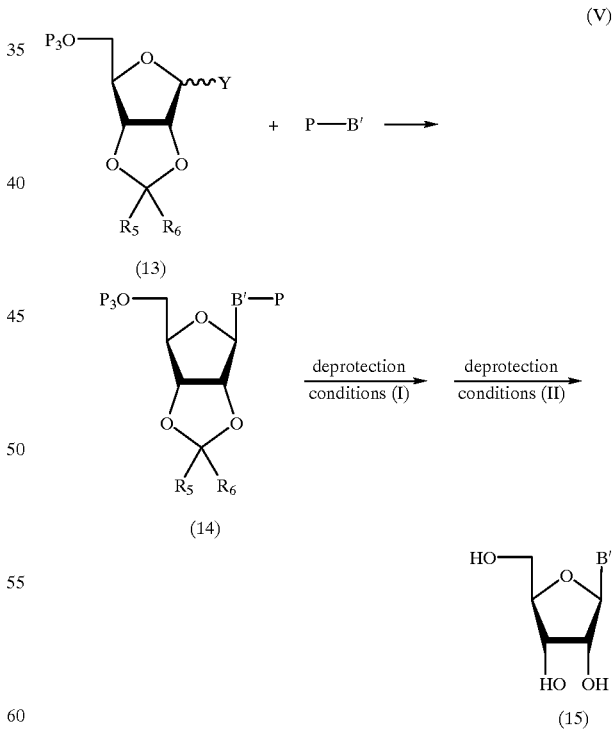

wherein:

Y, $R_5$ and $R_6$ are as defined previously;

$P_3$ is a base-stable hydroxyl protecting group, including, but not limited to, a group that may form an ester or ether of the hydroxyl; and P-B' is an appropriately protected purine or pyrimidine.

In reaction scheme (V), a protected β-ribosyl halide (13) is reacted with an appropriately protected purine or pyrimidine (p-B') to yield the respective protected β-ribopurine or β-ribopyrimidine (14). The 2',3'-O-alkylidene group, the 5' hydroxyl protection group P$_3$, and any protecting groups present on the purine or pyrimidine base (P) are subsequently removed in one or more deprotecting steps. The P$_3$ protecting group includes, but is not limited to, any of the conventional ether or ester forming protecting groups described supra and in Greene & Wuts, *Protective Groups in Organic Synthesis*, supra, provided that the protecting group is base-stable.

Nucleoside analogs synthesized by the methods of the present invention are useful reagents for the labeling, detection and analysis of nucleic acids. Additionally, the nucleoside analogs may be used to generate a combinatorial library of nucleoside analogs for the purpose of testing them for inhibitory activity against important macromolecular targets such as kinases, gyrases, and reverse transcriptase. Nucleoside analogs in the library that do possess inhibitory activity against such macromolecular targets could serve as lead compounds for the development of pharmaceuticals that relieve clinical indications, such as inflammation, or infectious diseases, such as, e.g., acquired immune deficiency syndrome, among many others.

Several of the nucleoside analogs synthesized by reaction scheme (III) have particular utility as adenosine kinase inhibitors. See e.g. U.S. Pat. No. 5,674,998. Adenosine kinase inhibitors show promise in treating neurological conditions such as seizures. (Id.). U.S. Pat. No. 5,674,998 discloses that 4-phenylamino-5-phenyl-7-(4-hydroxymethyl-1-β-D-ribofuranosyl)pyrrolo(2,3-d) pyrimidine, 4-N-(4-fluorophenylamino)-5-phenyl-7-(4-spirocyclopropyl-β-D-erythrofuranosyl)pyrrolo(2,3-d) pyrimidine and 4-phenylamino-5-phenyl-7-(1-β-D-erythrofuranosyl)-pyrrolo(2,3-d)pyrimidine are all nanomolar inhibitors of partially purified pig heart adenosine kinase. Additionally, several of the nucleoside analogs synthesized by Reaction (III) may be used to treat chronic pain.

The chemical structural formulae referred to herein may exhibit the phenomena of tautomerism, conformational isomerism, geometric isomerism and/or stereoisomerism. As the formulae drawings within this specification can only represent one of the possible tautomeric, conformational isomeric, geometric isomeric or stereoisomeric forms, it should be understood that the invention encompasses any tautomeric, conformational isomeric, geometric isomeric or stereoisomeric forms that exhibit biological or pharmacological activity as defined herein.

EXAMPLES

Example 1

Synthesis of 2,3 -O-isopropylidene-β-D-erythrofuranosyl chloride (10a)

where Y=Cl (10a), Y=Br (10b).

Intermediate 2,3-O-isopropylidene-D-erythrose 2,3-O-isopropylidene-D-erythrose was purchased from Pfansteihl, or prepared by diisobutylaluminum hydride reduction of 2,3-O-isopropylidene-D-erythronolactone according to the methods of Cohen et. al., 1983, *J. Am. Chem. Soc.*, 105, 3661–3672. The reagent 2,3-O-isopropylidene-D-erythronolactone is available from Aldrich or may be synthesized from iso-ascorbic acid as described in Organic Synthesis Coll. Vol. VII, page 297.

Title Compound

Synthesis of the title compound was performed according to the methods of Ireland et al., 1978,. *Org. Chem.*, 43, 786–787, and Lerner et al., 1969, *Carbohydr. Res.*, 9, 1–4. Specifically, a solution of 2,3-O-isopropylidene-D-erythrose (20.0 g, 125 mmol) in CH$_2$Cl$_2$ (250 mL) and pyridine (40 mL) was cooled in an ice/water bath. To the mixture, SOCl$_2$ (10 mL, 137.8 mmol) was added dropwise at such a rate that the internal temperature was kept below 5° C. (addition took 35 minutes). The disappearance of starting material was confirmed by removing an aliquot and checking the reaction by $^1$H NMR. Fifteen minutes after SOCl$_2$ addition was completed, the cold solution was added to H$_2$O (500 mL) and diisopropyl ether (500 mL). The layers were separated and the organic layer was extracted with 0.5 M HCl (500 mL) to remove remaining pyridine. The organic layer was then extracted with saturated NaHCO$_3$ (300 mL), and further dried over K$_2$CO$_3$. The solution was filtered and concentrated to provide 16.96 g (76%) of the title compound as a white crystalline solid.

mp=57.0–58.3° C. (Literature reported value (Lit.)= 60–61.5° C., Lit. of enantiomer 59–60° C.). [α]D: −167 (c 2.0, CH$_2$Cl$_2$) [Lit. [α]$_D$: −167 (c 0.8, CHCl$_3$), Lit. of enantiomer [α]$_D$: +168 (α2.0, CH$_2$Cl$_2$)] $^1$H NMR (300 MHz, d$_6$-DMSO): 1.28 (s, 3), 1.38 (s, 3), 4.05 (dd, 1, J=3.4, 10.9), 4.13 (d, 1, J=10.9), 4.95 (d, 1, J=5.9), 5.00 (dd, 1, J=3.3, 5.9), 6.46 (s, 1).

$^{13}$C NMR (75 MHz, d$_6$-DMSO): δ25.83, 27.16, 74.74, 79.38, 89.44, 101.07, 113.17. Anal. Calcd for C$_7$H$_{11}$O$_3$Cl: C, 47.07; H, 6.21. Found: C, 47.24; H, 6.20.

Example 2

Synthesis of 4-N-(4-fluorophenyl)amino-5-phenyl-1-(2,3-O isopropylidene-β-D-erythrofuranosyl) pyrrolo-(2,3-d)pyrimidine (CJ-19039)

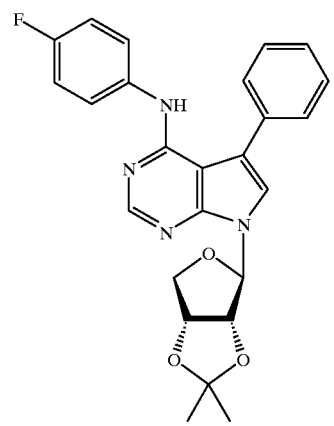

Intermediate 5-phenyl-4-N-(4-fluorophenyl)aminopyrrolo(2,3-d) pyrimidine

Syntesis of 5-phenyl-4-N-(4-fluorophenyl)aminopyrrolo-(2,3-d)pyrimidine was performed according to the methods of U.S. Pat. No. 5,674,998.

Title Compound

To a solution of 5phenyl-4-N-(4-flurophenyl) aminopyrrolo(2,3-d)pyrimidine (900 g, 29.6 mmol) in DMSO (75 mL), was added sodium t-butoxide (8.56 g, 89.1 mmol), causing a rise in internal temperature from 20° C. to 28° C. To the solution was added 2,3-O-isopropylidene-β-D-erythrofuranosyl chloride (compound 10a, 7.97 g, 44.6 mmol). The internal temperature rose from 26° C. to 44° C. over 2–3 minutes. After a total reaction time of 30 minutes, the solution was added to $H_2O$ (400 mL) and methyl t-butyl ether (275 mL). The phases were separated, and the organic layer was extracted with 0.5 M HCl (1×200 mL, 1× 100 mL), sat. aq. $NaHCO_3$ (100 mL), dried ($MgSO_4$), filtered, and concentrated to a yellow moist solid. To this material was added isopropyl ether (70 mL) and the heterogeneous mixture was heated to reflux for 2 hours. Upon cooling to 0° C., the solution was filtered and the solids rinsed with cold diisopropyl ether (75 mL) to provide (after drying) 6.2122 g (47%) of the title compound as a yellow powder. The HCl extractions had effectively removed all undesired N-1 alkylated heterocycle. For additional purity, the title compound could also be recrystallized from approximately 25 volumes of diisopropyl ether. The α:β anomeric ratio of the title compound was less than 1:100.

mp=143.0–144.1° C. $[\alpha]_D$: −77.2 (c 1.0, $CH_3COCH_3$)

$^1$H NMR (300 MHz, $d_6$-DMSO): δ1.33 (s, 3), 1.51 (s, 3), 4.08 (d, 1, J=10.6), 4.20 (dd, 1, J=3.7, 10.7), 5.29 (dd, 1, J=3.4, 5.8), 5.42 (d, 1, J=5.9), 6.32 (s, 1) 7.12–7.20 (m, 2), 7.40–7.47 (m, 1), 7.51–7.65 (m, 8), 8.39 (s, 1).

$^{13}$C NMR (75 MHz, $d_6$-DMSO): 24.79, 26.47, 74.38, 81.11, 84.47, 90.08, 101.93, 112.10, 115.40 (d, J=22), 116.21, 123.34 (d, J=8), 123.71, 127.47, 128.91, 129.23, 134.17, 135.80, 150.48, 151.41, 153.95, 158.06 (d, J=238).

Anal. Calcd for $C_{25}H_{23}N_4O_3F$: C, 67.25; H, 5.19; N, 12.55. Found: C, 67.11; H, 5.17; N, 12.60.

Mass Spec: AP+=447.2, AP−=445.2

Example 3

Synthesis of 4-N-(4-fluorophenyl)amino-5-phenyl-1-(2,3-O-isopropylidene-β-D-erythrofuranosyl) pyrrolo-(2,3-d)pyrimidine (CJ-19039) - Pilot Plant Scale The initial scale-up of this reaction on ~2 kilograms of 5-phenyl-4-N-(4-fluorophenyl)aminopyrrolo(2,3-d) pyrimidine was preceded by an ~500 gram pilot-run. The pure product of the pilot was combined with the reaction described below prior to final purification of the large reaction to provide one lot of product. The yield was adjusted to reflect the combination of the 500 g and 2 kg runs. The conditions for the two runs, other than scale, were identical. Thus, only the 2 kg run is described in detail below.

Intermediate 1

2,3-O-isopropylidene-D-erythrose 2,3-O-isopropylidene-D-erythrose was prepared according to the methods described in Example 1, supra.

Intermediate 2

2,3 -O-isopropylidene-β-D-erythrofuranosyl chloride (10a)

A solution of 2,3-O-isopropylidene-D-erythrose (2 kg, 12.5 mol) in tetrahydrofuran (THF) (19 L) and pyridine (1.1 L) was cooled to 0–5° C. To the mixture was slowly added $SOCl_2$ (960 mL, 13.1 mol) at such a rate that the internal temperature was kept below 15° C. This addition took 50 minutes. The disappearance of starting material was confirmed by removing an aliquot of the reaction and checking the aliquot by $^1$H NMR ten minutes after addition of $SOCl_2$ was complete. The solution was then filtered over 0.5 kg of celite, and rinsed with THF. This THF solution of the title compound was used crude in the coupling reaction to synthesize CJ-19039, as described below.

Intermediate 3

5-phenyl4-N-(4-fluorophenyl)aminopyrrolo(2,3-d)-pyrimidine

Synthesis of 5-phenyl-4-N-(4-fluorophenyl)aminopyrrolo (2,3-d)-pyrimidine was performed according to the methods of U.S. Pat. No. 5,674,998.

Title Compound

To a solution of 5-phenyl-4-N-(4-fluorophenyl) aminopyrrolo(2,3-d)-pyrimidine (2.2 kg, 7.23 mol) in DMSO (20 L), was added sodium t-butoxide (3.6 kg, 37.5 mol), causing a 5° C. exotherm. To the reaction solution was added the THF solution of 2,3-O-isopropylidene-β-D-erythrofuranosyl chloride (from above, theoretical 2.2 kg, 12.5 mol) over a period of 45 minutes. The reaction was allowed to stir overnight, then quenched into water (100 L) and methyl t-butyl ether (100 L). The phases were separated, and the organic layer extracted with 1 M HCl (3×25 L), and the organic layer filtered on a 4 kg silica gel pad. The filtrate was concentrated under atmospheric pressure to ~15 L, diisopropylether (70 L) was added, and the concentration continued to a final volume of ~30 L. At this point, 325 g of pure title compound from the ~500 g pilot-run was blended with the crude title compound before final crystallization. The solution was cooled to 0–5° C. to granulate, and filtered to provide 1.87 kg of the title compound (48% after subtraction of the 325 g addition of title compound from the ~500 g pilot run). The filtrate was concentrated, and taken up in methyl t-butyl ether (18 L). This organic layer was extracted with 1M HCl (4×3 L), and then concentrated to 2 L under atmospheric pressure. To the mixture was added diisopropyl ether (6 L) and the solution volume reduced to 4 L. After granulating at 0° C. for two hours, the solids were filtered off to provide 198 g (6%) of a second crop of the title compound, bringing the combined yield of the title compound for the ~2 kg run to 54%. The HCl extractions effectively removed all of the undesired N1-alkylated heterocycle.

Example 4

Synthesis of 4-N-(4-fluorophenyl)amino-5-phenyl-1-β-D-erythrofuranosyl)pyrrolo-(2,3-d)pyrimidine

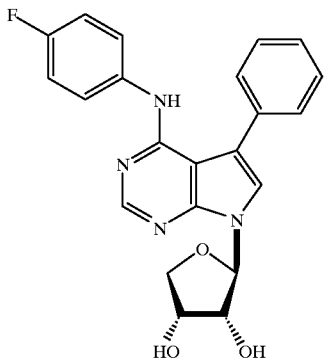

To a solution of CJ-19039 (Example 3, supra) (2.6680 g, 5.975 mmol) in isopropanol (15 mmol), was added 0.5 M HCl (15 mL). The hetergeneous solution was heates to 80° C. After 50 minutes, the solution was homogeneous. After a total of 3 hours at 80° C., Darco activated charcoal (360 mg) was added and heating was discontinued. After stirring 1.75 hours after addition of charcoal, the solution was filtered through celite, and the solids rinsed with 1:1 isopropanol:$H_2O$ (15 mL). The product was precipitated from the combined filtrates by adding 1M NaOH (7.5 mL) with rapid stirring, followed by $H_2O$ (20 mL) to aid in stirring the slurry. The solid was then filtered and the cake rinsed with $H_2O$ (15–20 mL). To the pasty, slightly pink powder was added 50 mL abs. EtOH, and the solution was heated to reflux. Hot ethanol was added in portions until all solids dissolved (total of 15 mL EtOH added over 15 min). The stirring was discontinued and the solution was allowed to slowly cool to room temperature. After cooling to room temperature, the flask was stored in the refrigerator (~0° C.) overnight to afford crystals. The crystals were then collected by filtration, and the solid rinsed with cold EtOH (20 ml) to provide 2.1044 g (87%) of the title compound as slightly pink crystals.

mp=194.8–195.2° C. $[\alpha]_D$:–91.7 (c, 1.0, $CH_3COCH_3$)

$^1$H NMR (300 MHz, $d_6$-DMSO): δ3.82 (d, 1, J=9.2), 4.24–4.3 1 (m, 1), 4.38 (dd, 1, J=3.7, 9.4), 4.70–4.78 (m, 1), 5.23 (d, 1, J=3.9), 5.44 (d, 1, J=6.7), 6.20 (d, 1, J=6.9), 7.15 (ap. t, 2, J=8.7), 7.42 (app t, 1, J=7.2), 7.50–7.66 (m, 7), 7.76 (s, 1), 8.40(s, 1).

$^{13}$C NMR (75 MHz, $d_6$-DMSO): δ70.56, 73.47, 74.99, 87.16, 102.03, 115.41 (d, J=22), 116.36, 122.17 (d, J=8), 122.74, 127.38, 128.88, 129.23, 134.38, 136.01, 151.27, 151.54, 153.92, 158.01 d, J=240).

Anal. Calcd for $C_{22}H_{19}N_4O_3F$: C, 65.02; H, 4.71; N, 13.79. Found: C, 64.96; H, 4.64; N, 13.92.

Mass Spec: AP+=407.1, AP-=405.2

The present invention is not to be limited in scope by the exemplified embodiments which are intended as illustrations of single aspects of the invention, and any compounds and methods for the use thereof which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. All references to stereochemistry, unless otherwise noted, are in strict reference to the α and β anomers of nucleosides and/or furanosyl halides.

All U.S. patents cited herein are hereby incorporated by reference in their entireties.

What is claimed is:

1. A method of making a 2',3'-O-alkylidene β-nucleoside analog, comprising reacting a 2',3'-O-alkylidene β-furanosyl halide having the structural formula:

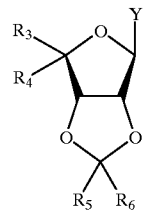

in which:

$R_3$ and $R_4$ are each independently selected from the group consisting of hydrogen, ($C_2$–$C_6$)alkenyl and ($CH_2$)$_n$Q, where n is an integer from 1 to 6;

or $R_3$ and $R_4$ together form a ring of from 3 to 6 carbons, the ring containing 0 to 3 heteroatoms selected from oxygen and nitrogen, and optionally substituted by one or more Q;

$R_5$ and $R_6$ are each independently selected from the group consisting of hydrogen, Q, ($C_1$–$C_6$) alkyl and ($C_1$–$C_6$) alkyl substituted with one or more Q;

Q is selected from the group consisting of hydrogen, —$NO_2$, —$N_3$, —CN, —$SR_7$, —$CX_3$, —$CF_3$, —X, —$OR_7$, —$C(O)OR_7$, —$C(O)R_7$, —$NR_7R_7$, —NH—$SO_2$—$R_7$, and —$SO_2R_7$;

each $R_7$ is independently selected from the group consisting of hydrogen, ($C_1$–$C_6$)alkyl, ($C_2$–$C_6$)alkenyl, ($C_5$–$C_{20}$)aryl, substituted ($C_5$–$C_{20}$)aryl, 5–20 membered heteroaryl, substituted 5–20 membered heteroaryl, and a protecting group;

X is halogen; and

Y is chloro or bromo;

with a heterocycle having a ring nitrogen capable of forming a covalent bond with the anomeric carbon of a furanose or furanose analog in dimethylsulfoxide (DMSO) or in a polar mixture of solvents comprising DMSO in the presence of a strong base.

2. The method of claim 1, wherein the molar ratio of the 2',3'-O-alkylidene β-furanosyl halide to the heterocycle is in the range of about 1:1 to about 3:1.

3. The method of claim 1, wherein the molar ratio of the strong base to the heterocycle is about 1:1 to about 8:1.

4. The method of claim 1, wherein the strong base is selected from the group consisting of sodium hydride, potassium hydride, sodium hydroxide, potassium hydroxide, sodium t-butoxide, sodium t-pentoxide, potassium t-butoxide and potassium t-pentoxide.

5. The method of claim 1, in which the 2',3'-O-alkylidene β-furanosyl halide has a structural formula selected from the group consisting of:

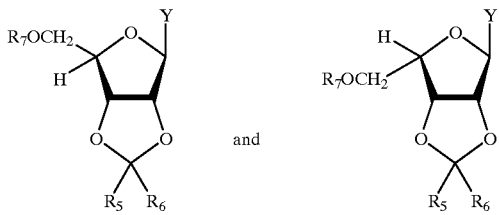

wherein $R_7$ is a protecting group.

6. The method of claim 1, in which the heterocycle has the structural formula:

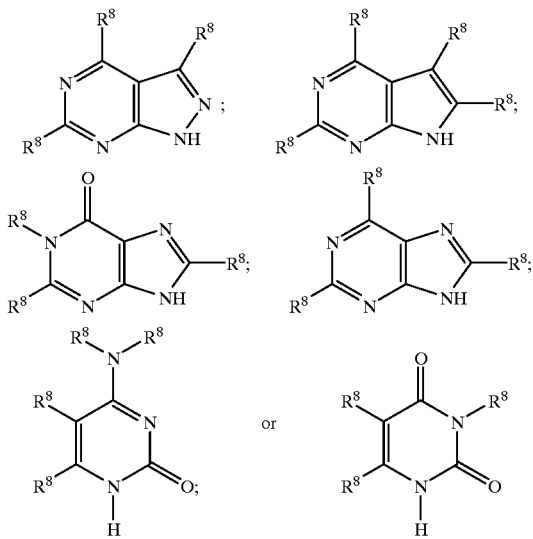

wherein each $R_8$ is independently selected from the group consisting of Q, $(C_1-C_6)$alkyl, $(C_1-C_6)$ alkyl substituted with one or more Q, $(C_5-C_{20})$aryl, $(C_5-C_{20})$aryl substituted with one or more Q, 5–20 membered heteroaryl, 5–20 membered heteroaryl substituted with one or more Q, $(C_6-C_{26})$alkaryl substituted with one or more Q, 6–26 membered alkheteroaryl, and 6–26 membered alkheteroaryl substituted with one or more Q;

Q is selected, from the group consisting of hydrogen, —$NO_2$, —$N_3$, —CN, —$SR_7$, —$CX_3$, —$CF_3$, —X, —$OR_7$, —C(O)$OR_7$, —C(O)$R_7$, —$NR_7R_7$, —NH—$SO_2$—$R_7$, and —$SO_2R_7$;

each $R_7$ is independently selected from the group consisting of hydrogen, $(C_1-C_6)$alkyl, $(C_2-C_6)$alkenyl, $(C_5-C_{20})$aryl, substituted $(C_5-C_{20})$aryl, 5–20 membered heteroaryl, substituted 5–20 membered heteroaryl, and a protecting group; and X is halogen.

7. The method of claim 1 in which $R_3$ and $R_4$ are each hydrogen.

8. The method of claim 1, wherein $R_5$ and $R_6$ are each methyl.

9. The method of claim 1, wherein the reaction is carried out in DMSO.

10. The method of claim 1, wherein the 2′,3′-O-alkylidene β-furanosyl halide is 2,3-O-isopropylidene-β-D-erythrofuranosyl chloride.

11. The method of claim 1, wherein the solvent mixture comprises DMSO and a solvent selected from the group consisting of N,N-dimethylformamide (DMF), acetonitrile, tetrahydrofuran (THF) and methyl t-butyl ether (MTBE).

12. The method of claim 1, wherein the percent volume of DMSO in the solvent mixture is at least about 15%.

13. The method of claim 11, wherein the solvent or solvent mixture is 1 part DMSO mixed with about 0 to 3 parts of a solution comprising one or more solvents selected from the group consisting of DMF, acetonitrile, THF, and MTBE.

14. The method of claim 11, wherein the solvent or solvent mixture is selected from the group consisting of DMSO, 1:1 (v/v) DMSO:acetonitrile, 1:1 DMSO:THF, 1:1 DMSO:MTBE, and 1:3 DMSO:MTBE.

15. The method of claim 1, further comprising the step of removing the 2′,3′-O-alkylidene group under acidic conditions in the presence of a hydroxylic solvent to yield the β-nucleoside analog.

16. The method of claim 1, wherein the heterocycle has the structural formula:

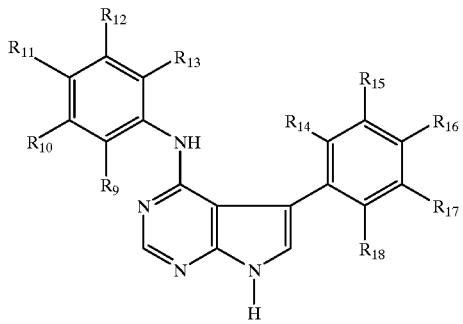

wherein:

$R_9$, $R_{10}$, $R_{11}$, $R_{12}$, $R_{13}$, $R_{14}$, $R_{15}$, $R_{16}$, $R_{17}$, and $R_{18}$, are each independently selected from the group consisting of Q, $(C_1-C_6)$alkyl, $(C_1-C_6)$alkyl substituted with one or more Q, $(C_1-C_{20})$ aryl, $(C_5-C_{20})$aryl substituted with one or more Q, 5–20 membered heteroaryl, 5–20 membered heteroaryl substituted with one or more Q, $(C_6-C_{26})$alkaryl, $(C_6-C_{26})$alkaryl substituted with one or more Q, 6–26 membered alkheteroaryl, and 6–26 membered alkheteroaryl substituted with one or more Q;

Q is selected from the group consisting of hydrogen, —$NO_2$, —$N_3$, —CN, —$SR_7$, —$CX_3$, —$CF_3$, —X, —$OR_7$, —C(O)$OR_7$, —C(O)$R_7$, —$NR_7R_7$, —NH—$SO_2$—$R_7$, and —$SO_2R_7$;

each $R_7$ is independently selected from the group consisting of hydrogen, $(C_1-C_6)$ alkyl, $(C_2-C_6)$alkenyl, $(C_5-C_{20})$aryl, substituted $(C_5-C_{20})$aryl, 5–20 membered heteroaryl, substituted 5–20 membered heteroaryl, and a protecting group;

and X is halogen.

17. The method of claim 16, wherein $R_9$, $R_{10}$, $R_{11}$, $R_{12}$, and $R_{13}$ are each independently selected from the group consisting of hydrogen, halogen, —$NH_2$, —$NO_2$, —CN, —$CF_3$ and —$OCH_3$; and $R_{14}$, $R_{15}$, $R_{16}$, $R_{17}$, and $R_{18}$ are each hydrogen.

18. The method of claim 16, wherein $R_{11}$ is fluoro and $R_9$, $R_{10}$, $R_{12}$ and $R_{13}$ are each hydrogen.

19. The method of claim 1, wherein the heterocycle is 5-phenyl-4-N-(4-fluorophenyl)aminopyrrolo(2,3-d)pyrimidine.

20. The method of claim 1, wherein the 2′,3′-O-alkylidene β-furanosyl halide is 2,3-O-isopropylidene-β-D-erythrofuranosyl chloride; the heterocycle is 5-phenyl-4-N-(4-fluorophenyl)aminopyrrolo(2,3-d)pyrimidine; and the solvent is DMSO.

* * * * *